United States Patent
Carr et al.

(10) Patent No.: US 12,371,749 B2
(45) Date of Patent: *Jul. 29, 2025

(54) MOLECULAR PATHOGENESIS OF MICROCARCINOMA OF THE THYROID

(71) Applicant: University of Vermont and State Agricultural College, Burlington, VT (US)

(72) Inventors: Frances Carr, Burlington, VT (US); Nikoletta Sidiropoulos, Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/515,938

(22) Filed: Nov. 1, 2021

(65) Prior Publication Data

US 2022/0056539 A1    Feb. 24, 2022

Related U.S. Application Data

(63) Continuation of application No. 15/788,305, filed on Oct. 19, 2017, now Pat. No. 11,162,141.

(60) Provisional application No. 62/410,119, filed on Oct. 19, 2016.

(51) Int. Cl.
C12Q 1/68 (2018.01)
C12Q 1/6886 (2018.01)

(52) U.S. Cl.
CPC ............ *C12Q 1/6886* (2013.01); *C12Q 1/68* (2013.01); *C12Q 2600/106* (2013.01); *C12Q 2600/158* (2013.01); *C12Q 2600/178* (2013.01)

(58) Field of Classification Search
CPC ............ C12Q 1/6886; C12Q 2600/106; C12Q 2600/158; C12Q 2600/178
See application file for complete search history.

(56) References Cited

U.S. PATENT DOCUMENTS 11,162,141 B2 * 11/2021 Carr ..................... C12Q 1/6886
2013/0142728 A1    6/2013 Beaudenon-Huibregtse et al.

OTHER PUBLICATIONS

Taguchi et al., "Principal Component Analysis Based Feature Extraction Approach to Identify Circulating microRNA Biomarks." PLOS ONE, Jun. 2013, vol. 8, Issue 6, e66714, pp. 1-12.
Van Rooij, Eva, "The Art of MicroRNA Research." Circulation Research (2011) vol. 108, pp. 219-234.
Wang et al., "RNA-Seq: a revolutionary tool for transcriptomics." Nature Reviews Genetics, (2009), vol. 10, Issue 1, pp. 57-63.
Lee et al. Cancer(2013) 119(24), 4358-4365. (Year: 2013).
Liu et al. (Acta Biochimica et Biophysica Sinica (2014) 46(2), pp. 92-99). (Year: 2014).
Jiang et al. Int. J. Cancer (2015) 136(4), 854-862, epub Jul. 2014. (Year: 2014).
Backes et al., Anal Chem. (2015) 87(17) p. 8910-8916.

* cited by examiner

*Primary Examiner* — J. E. Angell
(74) *Attorney, Agent, or Firm* — Pierce Atwood LLP

(57) ABSTRACT

The invention relates, in part, to compounds, compositions, and methods to assess molecular characteristics papillary microcarcinoma (PMC) of the thyroid and indicators of indolent compared to aggressive PMC of the thyroid. In addition, the invention relates, in part, to methods of assessing characteristics of microRNAs associated with PMC of the thyroid.

7 Claims, 4 Drawing Sheets

Indolent Signature

Confirmed increase

Did not confirm decrease

Aggressive Signature

Confirmed increase

Confirmed decrease

Confirmed decrease

Confirmed decrease

Confirmed decrease

Confirmed decrease

MOLECULAR PATHOGENESIS OF MICROCARCINOMA OF THE THYROID

RELATED APPLICATIONS

This application is a continuation under 35 U.S.C. § 120 of U.S. patent application Ser. No. 15/788,305 filed on Oct. 19, 2017, and claims benefit under 35 U.S.C. § 119 (e) of U.S. Provisional Application No. 62/410,119, filed Oct. 19, 2016, the content of each of which is incorporated by reference herein in its entirety.

FIELD OF THE INVENTION

The invention relates, in part, to compounds, compositions, and methods to assess characteristics of microcarcinoma of the thyroid. In addition, the invention relates, in part, to assays to assess microRNAs associated with microcarcinomas of the thyroid.

BACKGROUND OF THE INVENTION

Papillary microcarcinoma of the thyroid gland (PMC) has a disease-specific mortality of <1% leading to suggestions that PMC may require no therapy. Yet the uncertainty of metastatic disease has led to relatively uniform management according to current guidelines that may result in over, or under treatment. PMC accounts for approximately half of the thyroid cancers diagnosed in the United States and Europe in the past three decades. Given the ATA guidelines and the potential risk of metastatic disease negatively impacting survival, most patients with this tumor ultimately have surgery and neck dissection to remove cervical lymph nodes, although central neck dissection increases the morbidity of thyroid surgery. Currently decisions to proceed or abstain from thyroid surgery are often made without sufficient evidence of how an individual cancer will behave over time.

SUMMARY OF THE INVENTION

According to an aspect of the invention, methods of selecting a treatment for a subject are provided. The methods including (a) obtaining a biological sample from a subject believed at risk for a microcarcinoma of the thyroid; (b) contacting the biological sample with one or more agents under suitable conditions to determine at least one characteristic of from 1 to 15 of the microRNAs: miR-146b, miR-138-1-3p, miR-3065-5p, miR-4484, miR-6780b-5p, miR-1185-1-3p, miR-3175, miR-4721, miR-3165-5p, miR-16-5p, miR-1991-3p, miR-96-5p, miR-15b-5p, miR-1271-5p, and miR-199b-3p; (c) determining at least one characteristic of each of the from 1 to 15 miRNAs in the sample; and (d) selecting a treatment for the subject based at least in part on the determined characteristic of the from 1 to 15 miRNAs. In some embodiments, the method also includes treating the subject with one or more of the selected treatments. In certain embodiments, the means for determining the at least one characteristic of the specific miRNA in the sample comprises one or more of: microarray analysis, deep sequencing, polymerase chain reaction (PCR), real time PCR, northern blotting, in situ hybridization, RNA-seq, and qPCR. In some embodiments, the agent comprises one or more of a microarray probe, a probe, a primer, a polynucleotide molecule, a detectable label, an enzyme, a buffer, a radioisotope, a dye, and an oligonucleotide. In some embodiments, (i) each agent when contacted with the from 1 to 15 miRNAs specifically binds a predetermined one of the from 1 to 15 miRNAs and forms a bound complex comprising the agent and the predetermined miRNA; (ii) determining a characteristic of at least one of the from 1-15 miRNAs in step (c) comprises determining a characteristic of one or more of the bound complexes; and (iii) selecting a treatment for the subject in step (d) is based at least in part the determined characteristic of the one or more bound complexes. In certain embodiments, the characteristic of the bound complex is one or more of: (i) presence or absence of the bound complex and (ii) a level of the bound complex. In some embodiments, a means of determining the characteristic of the bound complex comprises measuring the level of the bound complex. In some embodiments, a level of the bound complex that is greater than zero determines that the miRNA that the agent specifically binds is present in the biological sample and a level of the bound complex equal to zero determines that the miRNA that the agent specifically binds is not present in the biological sample. In certain embodiments, the method also includes using the determined presence of the from 1 to 15 miRNAs to assist in identifying the presence and type of a microcarcinoma of the thyroid in the subject. In some embodiments, the presence of at least one of miR-146b and miR-138-1-3p indicates an indolent microcarcinoma of the thyroid. In some embodiments, the presence of at least one of miR-3065-5p, miR-4484, miR-6780b-5p, miR-1185-1-3p, miR-3175, miR-4721, miR-3165-5p, miR-15b-5p, miR-1271-5p, and miR-199b-3p indicates an aggressive microcarcinoma of the thyroid. In some embodiments, the treatment comprises one or more of: surgery, radiation, chemotherapy, administration of a pharmaceutical agent, abstention from surgery, abstention from radiation, abstention from chemotherapy, and abstention from administration of a pharmaceutical agent. In certain embodiments, the biological sample comprises one or more of: tissue, blood, serum, saliva, and lymph fluid. In some embodiments, the microcarcinoma is papillary microcarcinoma. In some embodiments, the microcarcinoma of the thyroid is an indolent microcarcinoma. In certain embodiments, the microcarcinoma of the thyroid is an aggressive microcarcinoma. In some embodiments, the subject is a mammal. In some embodiments, the subject is a human. In certain embodiments, the miRNA is at least one of miR-146b and miR-138-1-3p. In some embodiments, the miRNA is at least one of miR-3065-5p, miR-4484, miR-6780b-5p, miR-1185-1-3p, miR-3175, miR-4721, miR-3165-5p, miR-15b-5p, miR-1271-5p, and miR-199b-3p. In some embodiments, the miRNA is at least one of: miR-16-5p, miR-1991-3p, and miR-96-5p. In certain embodiments, the miRNA is at least one of miR-532-3p, miR-3607-5p, miR-574-3p, miR-26b-5p, miR-199b-5p, miR-487b-3p, miR-199a-3p, and miR-766-3p. In some embodiments, the miRNA is at least one of miR-21-5p, miR-34a-5p, miR-222-3p, miR-221-3p, miR-221-5p, miR-551b-3p, miR-146b-3p, miR-146b-5p, and miR-375. In certain embodiments, the miRNA is at least one of miR-15b-5p, miR-1271-5p, and miR-199b-3p. In some embodiments, the subject is a mammal. In some embodiments, the subject is a vertebrate. In certain embodiments, in some embodiments the subject is a human. In some embodiments, the method also includes determining in the biological sample one or more of (i) presence or absence and (ii) a level of an miRNA that is not one of the from 1-15 miRNAs. In some embodiments, the method also includes using the determination to aid in selection of a treatment for the subject. In certain embodiments, the method also includes treating the subject with one or more of the selected treatments. In some embodiments, one or more of: (i) an increase in a level of miR-146b in the biological sample compared to a normal or control level and (ii) a decrease in level of miR-138-1-3p in the biological sample compared to a normal or control level indicates that the microcarcinoma of the thyroid is an indolent microcarcinoma. In some embodiments, one or more of: (i) an increase in a level of one or more of miR-3065-5p, miR-15b-5p, miR-1271-5p, and miR-199b-3p in the biological sample compared to a normal or control level and (ii) a decrease in one or more of: miR-4484, miR-6780b-5p, miR-1185-1-3p, miR-3175, miR-4721, and miR-3165-5p in the biological sample compared to a normal or control level indicates that the microcarcinoma of the thyroid is an aggressive microcarcinoma.

According to another aspect of the invention, methods of assessing one or more characteristics of a bound complex that includes an agent selectively bound to a microRNA (miRNA) molecule are provided, the methods including: (a) contacting a biological sample with an agent under suitable conditions for the agent to specifically bind to an miRNA of and form a bound complex comprising the agent and the miRNA, wherein the miRNA is miR-146b, miR-138-1-3p, miR-3065-5p, miR-4484, miR-6780b-5p, miR-1185-1-3p, miR-3175, miR-4721, miR-3165-5p, miR-16-5p, miR-1991-3p, miR-96-5p, miR-15b-5p, miR-1271-5p, or miR-199b-3p; and (b) determining at least one characteristic of the bound complex in the biological sample. In certain embodiments, the method also includes performing steps (a) and (b) with one or more additional agents that selectively bind to one or more of the miRNAs. In some embodiments, a means for determining the at least one characteristic of the specific miRNA in the sample comprises one or more of: microarray analysis, deep sequencing, polymerase chain reaction (PCR), real time PCR, northern blotting, in situ hybridization, RNA-seq, and qPCR. In some embodiments, the agent comprises one or more of a microarray probe, a probe, a primer, a polynucleotide molecule, a detectable label, an enzyme, a buffer, a radioisotope, a dye, and an oligonucleotide. In certain embodiments, the characteristic of the bound complex is one or more of: the presence or absence of the bound complex, and a level of the bound complex. In some embodiments, a means of determining the characteristic of the bound complex comprises measuring the level of the bound complex. In some embodiments, a level of the bound complex that is greater than zero determines that the miRNA that the agent specifically binds is present in the biological sample and a level of the bound complex equal to zero determines that the miRNA that the agent specifically binds is not present in the biological sample. In certain embodiments, the miRNA is one of miR-146b and miR-138-1-3p. In some embodiments, the miRNA is one of miR-3065-5p, miR-15b-5p, miR-1271-5p, miR-199b-3p, miR-4484, miR-6780b-5p, miR-1185-1-3p, miR-3175, miR-4721, and miR-3165-5p. In some embodiments, the miRNA is one of: miR-16-5p, miR-1991-3p, and miR-96-5p. In some embodiments, the method also includes contacting the biological sample with one or more agents that bind: miR-532-3p, miR-3607-5p, miR-574-3p, miR-26b-5p, miR-199b-5p, miR-487b-3p, miR-199a-3p, or miR-766-3p. In certain embodiments, the method also includes contacting the biological sample with one or more agents that bind: miR-21-5p, miR-34a-5p, miR-222-3p, miR-221-3p, miR-221-5p, miR-551b-3p, miR-146b-3p, miR-146b-5p, or miR-375. In some embodiments, the method also includes contacting the biological sample with one or more of agents that bind miR-15b-5p, miR-1271-5p, or miR-199b-3p. In some embodiments, the method also includes obtaining the biological sample from a subject. In certain embodiments, the subject is a mammal. In some embodiments, the subject is a vertebrate. In some embodiments, the subject is a human. In some embodiments, the method also includes using the determined presence of the bound complex to assist in identifying the presence and type of a microcarcinoma of the thyroid in the subject. In certain embodiments, the presence of a bound complex comprising one of miR-146b and miR-138-1-3p indicates an indolent microcarcinoma of the thyroid. In some embodiments, the presence of a bound complex comprising one of miR-3065-5p, miR-15b-5p, miR-1271-5p, miR-199b-3p, miR-4484, miR-6780b-5p, miR-1185-1-3p, miR-3175, miR-4721, and miR-3165-5p indicates an aggressive microcarcinoma of the thyroid. In some embodiments, the method also includes using the determined presence of the bound complex to assist in one or more of: selecting a treatment for the subject and treating the subject. In certain embodiments, the treatment comprises one or more of: surgery, radiation, chemotherapy, administration of a pharmaceutical agent, abstaining from surgery, abstaining from radiation, abstaining from chemotherapy, and abstaining from administration of a pharmaceutical agent. In some embodiments, the method also includes determining in the sample one or more of (i) presence or absence and (ii) a level of an miRNA that is not one of: miR-146b, miR-138-1-3p, miR-3065-5p, miR-15b-5p, miR-1271-5p, and miR-199b-3p, miR-4484, miR-6780b-5p, miR-1185-1-3p, miR-3175, miR-4721, miR-3165-5p, miR-16-5p, miR-1991-3p, and miR-96-5p. In some embodiments, the method also includes using the determination to aid in the selection of a treatment for the subject. In certain embodiments, the method also includes treating the subject with one or more of the selected treatments. In some embodiments, one or more of: (i) an increase in a level of miR-146b in the biological sample compared to a normal or control level and (ii) a decrease in level of miR-138-1-3p in the biological sample compared to a normal or control level indicates that the microcarcinoma of the thyroid is an indolent microcarcinoma. In some embodiments, one or more of: (i) an increase in a level of one or more of miR-3065-5p, miR-15b-5p, miR-1271-5p, and miR-199b-3p in the biological sample compared to a normal or control level and (ii) a decrease in one or more of: miR-4484, miR-6780b-5p, miR-1185-1-3p, miR-3175, miR-4721, and miR-3165-5p in the biological sample compared to a normal or control level indicates that the microcarcinoma of the thyroid is an aggressive microcarcinoma.

According to another aspect of the invention, methods of preparing a bound complex comprising an miRNA and an agent that specifically binds the miRNA are provided, the methods including contacting a sample believed to be at risk of containing at least one miRNA of: miR-146b, miR-138-1-3p, miR-3065-5p, miR-15b-5p, miR-1271-5p, miR-199b-3p, miR-4484, miR-6780b-5p, miR-1185-1-3p, miR-3175, miR-4721, miR-3165-5p, miR-16-5p, miR-1991-3p, and miR-96-5p; with one or more agents that each specifically binds one of the miRNAs, wherein the contacting is under conditions suitable for the one or more agents to specifically bind its miRNA and form a bound complex. In some embodiments, the agent comprises one or more of a microarray probe, a probe, a primer, a polynucleotide molecule, a detectable label, an enzyme, a buffer, a radioisotope, a dye, and an oligonucleotide. In certain embodiments, the method also includes determining at least one characteristic of the miRNA present in the bound complex, wherein a means for determining the at least one characteristic of the miRNA comprises one or more of: microarray analysis, deep sequencing, polymerase chain reaction (PCR), real time PCR, northern blotting, in situ hybridization, RNA-seq, and qPCR. In certain embodiments, the characteristic of the bound complex is one or more of: presence or absence of the bound complex and a level of the bound complex. In some embodiments, a means of determining the characteristic of the bound complex comprises measuring the level of the bound complex. In some embodiments, a level of the bound complex that is greater than zero determines that the miRNA that the agent specifically binds is present in the sample and a level of the bound complex equal to zero determines that the miRNA that the agent specifically binds is not present in the sample. In certain embodiments, the method also includes determining a characteristic of the bound complex in the contacted sample. In some embodiments, the miRNA is one of miR-146b and miR-138-1-3p. In some embodiments, the miRNA is one of miR-3065-5p, miR-15b-5p, miR-1271-5p, miR-199b-3p, miR-4484, miR-6780b-5p, miR-1185-1-3p, miR-3175, miR-4721, and miR-3165-5p. In certain embodiments, the miRNA is one of: miR-16-5p, miR-1991-3p, and miR-96-5p. In some embodiments, the method also includes use of or using the determined presence of the bound complex to assist in identifying the presence and type of a microcarcinoma of the thyroid in the sample. In some embodiments, the presence of a bound complex comprising one of miR-146b and miR-138-1-3p identifies an indolent microcarcinoma of the thyroid. In certain embodiments, the presence of a bound complex comprising one of miR-3065-5p, miR-15b-5p, miR-1271-5p, miR-199b-3p, miR-4484, miR-6780b-5p, miR-1185-1-3p, miR-3175, miR-4721, and miR-3165-5p identifies an aggressive microcarcinoma. In some embodiments, the sample is a biological sample. In some embodiments, the biological sample comprises tissue, blood, saliva, lymph, and CSF. In some embodiments, the biological sample is obtained from a subject. In certain embodiments, the subject is a mammal. In some embodiments, the subject is a vertebrate. In some embodiments, the subject is a human. In certain embodiments, the method also includes using the determined presence of the bound complex to assist in one or more of: selecting a treatment for the subject and treating the subject. In some embodiments, the treatment comprises one or more of: surgery, radiation, chemotherapy, administration of a pharmaceutical agent, abstaining from surgery, abstaining from radiation, abstaining from chemotherapy, and abstaining from administration of a pharmaceutical agent. In some embodiments, the method also includes determining in the sample one or more of (i) presence or absence and (ii) a level of an miRNA that is not one of: miR-146b, miR-138-1-3p, miR-3065-5p, miR-15b-5p, miR-1271-5p, miR-199b-3p, miR-4484, miR-6780b-5p, miR-1185-1-3p, miR-3175, miR-4721, miR-3165-5p, miR-16-5p, miR-1991-3p, and miR-96-5p. In certain embodiments, the method also includes using the determination to aid in selecting a treatment for the subject. In some embodiments, the method also includes treating the subject with one or more of the selected treatments. In some embodiments, one or more of: (i) an increase in a level of miR-146b in the biological sample compared to a normal or control level and (ii) a decrease in level of miR-138-1-3p in the biological sample compared to a normal or control level indicates that the microcarcinoma of the thyroid is an indolent microcarcinoma. In an embodiments, one or more of: (i) an increase in a level of one or more of miR-3065-5p, miR-15b-5p, miR-1271-5p, and miR-199b-3p, in the biological sample compared to a normal or control level and (ii) a decrease in one or more of: miR-4484, miR-6780b-5p, miR-1185-1-3p, miR-3175, miR-4721, and miR-3165-5p in the biological sample compared to a normal or control level indicates that the microcarcinoma of the thyroid is an aggressive microcarcinoma.

According to another aspect of the invention, kits are provided that include (i) from 1 to 15 agents that specifically bind to from 1 to 15 miRNAs, respectively, wherein the 1-15 miRNAs include: miR-146b, miR-138-1-3p, miR-3065-5p, miR-15b-5p, miR-1271-5p, miR-199b-3p, miR-4484, miR-6780b-5p, miR-1185-1-3p, miR-3175, miR-4721, miR-3165-5p, miR-16-5p, and miR-1991-3p, and miR-96-5p; (ii) one or more positive and negative controls miRNA binding agents; (iii) instructions for contacting a biological sample with the from 1 to 15 agents and control miRNAs under suitable conditions for the agents to selectively bind the miRNAs, and (iv) optionally instructions for determining at least one characteristic of the from 1 to 15 miRNAs in the sample. In some embodiments, the kit also includes one or more additional agents that bind to one or more miRNAs, respectively.

BRIEF DESCRIPTION OF THE DRAWINGS

FIG. 1A shows a Venn diagram: illustrating differentially expressed noncoding RNAs (ncRNAs), unique and shared between indolent and aggressive PMC compared to matched uninvolved tissue. Left circle represents Indolent tumor vs matched normal (18). Right circle represents aggressive tumor vs matched normal (34). FIG. 1B provides diagram of principal component analysis: patient-matched aggressive tumor (left ellipse); normal (uppermost ellipse); and metastatic tissues (lower, rightmost ellipse) captures differential ncRNA profiles FIG. 2 provides a diagram illustrating differential microRNA expression in papillary microcarcinomas of the thyroid. Results filtered at significance of p<0.05 and at least 2-fold higher or lower expression. As show in the "Predictors of aggressive Tumors" section, at least 2-fold higher was determined for: miR-532-3p, miR-199b-5p, miR-3607-5p, miR-487b-3p, miR-574-3p, miR-199a-3p, miR-26b-5p, and miR-766-3p. As shown in the "Development of Neoplasia" section, at least 2-fold higher was determined for: miR-21-5p, miR-34a-5p, miR-222-3p, miR-221-3p, miR-221-5p, miR-551b-3p, miR-146b-3p, miR-146-5p, and miR-375. As shown under the "Indolent Tumor Signature" heading at least 2-fold higher was determined for miR146b and at least 2-fold lower was determined for miR-138-1-3p. As shown under the "Aggressive Tumor Signature" heading at least 2-fold higher was determined for miR-3065-5p, miR-15b-5p, miR-1271-5p, and miR-199b-3p; and at least 2-fold lower was determined for: miR-4484, miR-6780b-5p, miR-1185-1-3p, miR-3175, miR-4721, and miR-3156-5p.

FIG. 3A illustrates results that confirmed an increase in hsa-miR-146-5p in indolent signature. FIG. 3B illustrates results that did not confirm a decrease in hsa-miR-138-1-3p. "T" is indolent primary tumor tissue and "N" is the matched normal tissue. "AT" is aggressive primary tumor tissue and "AN" is the matched normal tissue.

DETAILED DESCRIPTION

Figures 1A, 1B:
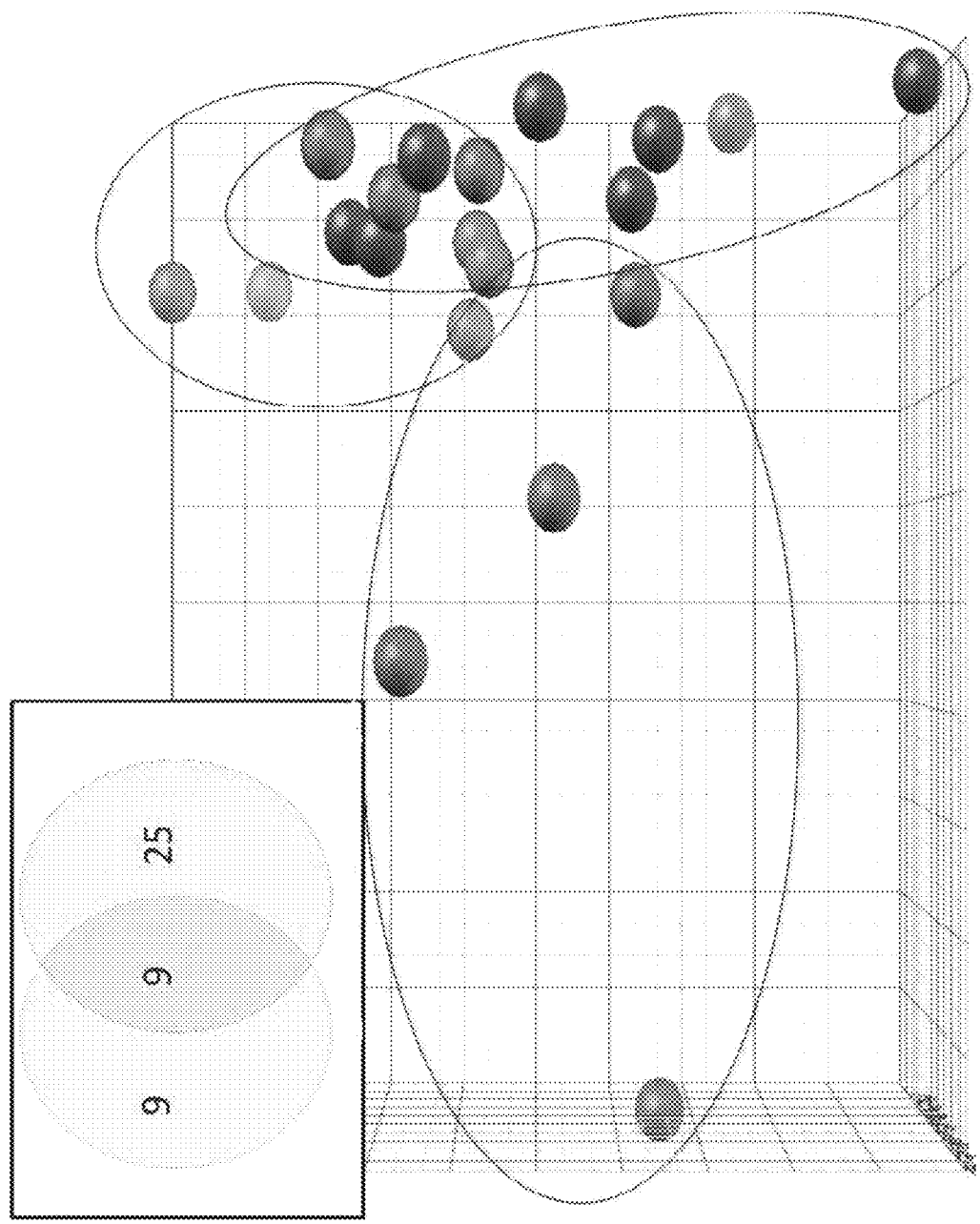
FIG. 1A-B provides a schematic diagram.

The invention provides predictive and prognostic parameters to assist in tailoring the treatment of PMC of the thyroid in individual patients with this disease. Methods for determining distinct molecular mechanisms underlying indolent and aggressive papillary microcarcinoma (PMC) of the thyroid gland have now been determined. The invention, in part, provides parameters that can be used to select treatments for PMC and to guide interventional management. Specific short noncoding (ncRNA) profiles have now been assessed and signature profiles for indolent and signature profiles for aggressive PMC of the thyroid have now been identified.

The invention is based, in part, on the discovery that an increase or decrease in certain, now identified, microRNAs (also referred to herein interchangeably as "miRNAs" and "miRs") in PMC can be used to determine whether a subject with the PMC of the thyroid has an aggressive PMC or an indolent PMC. An aggressive PMC presents a high risk of metastatic spread of the cancer and increased likelihood of death. An indolent PMC indicates an increased likelihood that the PMC will not result in metastatic spread. Based on the severe prognosis for aggressive PMC of the thyroid versus less severe prognosis for indolent PMC of the thyroid, methods of the invention can be used to select treatments that are tailored to indolent or aggressive PMC of the thyroid.

Indolent and Aggressive PMC

An indolent carcinoma is one that grows slowly and may not require extensive, or in some instances, any therapeutic intervention. Aggressive carcinomas grow and spread more quickly than indolent cancers and are candidates for more extensive therapeutic intervention.

Methods to characterize indolent and aggressive PMCs of the thyroid have now been identified and a status of a PMC of the thyroid as indolent or its status as aggressive can be determined using methods of the invention. Methods of the invention include but are not limited to one or more of: (1) determining the presence or absence of 1, 2, 3, 4, 5, 6, 7, 8, 9, 10, 11, 12, 13, 14, 15, or more miRNAs that have been determined as indicative of PMC status and (2) determining an amount or level of the 1, 2, 3, 4, 5, 6, 7, 8, 9, 10, 11, 12, 13, 14, 15, or more miRNAs. In some aspects of the invention characteristics of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or more miRNAs are assessed. As used herein the term "characteristics of an miRNA" means one or both of the characteristics (1) and (2) listed above herein.

miRNAs that have been identified as associated with the status of a PMC of the thyroid and whose characteristics can be determined in methods of the invention are: miR-146b, miR-138-1-3p, miR-3065-5p, miR-15b-5p, miR-1271-5p, miR-199b-3p, miR-4484, miR-6780b-5p, miR-1185-1-3p, miR-3175, miR-4721, miR-3165-5p, miR-16-5p, miR-1991-3p, and miR-96-5p. Methods of the invention can be used to determine a characteristic of 1, 2, 3, 4, 5, 6, 7, 8, 9, 10, 11, 12, 13, 14, or 15 of these miRNAS in a biological sample. The 1, 2, 3, 4, 5, 6, 7, 8, 9, 10, 11, 12, 13, 14, or 15 miRNAs may also be referred to herein as "predetermined miRNAs" indicating, for example that their presence and/or level are specifically assessed in a sample, which may comprise use of an agent that selectively binds to a predetermined miRNA. Sequences of miRNAs including those described herein are available at miRBASE, http://mir-base.org/.

It will be understood assessing characteristics of different combinations of 2, 3, 4, 5, 6, 7, 8, 9, 10, 11, 12, 13, 14, 15 miRNAs that have been identified as associated with the status of a PMC of the thyroid can be included in some embodiments of the invention. As non-limiting examples, a method of the invention may comprise assessing one or more characteristics of one or more of the following combinations: (1) miR-146b, miR-138-1-3p, miR-3065-5p, and miR-4484; (2) miR-146b, miR-138-1-3p, miR-3065-5p, miR-6780b-5p, and miR-4484; (3) miR-146b, miR-138-1-3p, miR-1271-5p, miR-199b-3p, miR-4721, and miR-3165-5p; (4) miR-146b, miR-138-1-3p, miR-199b-3p and miR-3175; and (5) miR-146b, miR-138-1-3p, miR-1271-5p, miR-3065-5p, and 1, 2, 3, 4, 5, or 6 of miR-4484, miR-6780b-5p, miR-1185-1-3p, miR-3175, miR-4721, and miR-3165-5p. Certain embodiments of the invention include methods comprising assessing a combination (1)-(5) or another combination based on information provided herein. It will be understood that in addition to assessing a combination of miRNAs set forth herein, methods of the invention may additionally include assessment of miRNAs in addition to those set forth herein.

Characteristics of miRNAs can be compared to control characteristics to determine the status of a PMC as indolent or aggressive. In some embodiments, methods of the invention, can be used to select a treatment for a subject with PMC, wherein the treatment is tailored to whether the subject's PMC is indolent or aggressive. In some aspects of the invention, treatments for indolent microcarcinoma is selected based in part of a determination that there is one or more of: (i) an increase in a level of miR-146b in a sample obtained from a subject compared to a normal or control level and (ii) a decrease in level of miR-138-1-3p in the sample from the subject compared to a normal or control level. In some aspects of the invention, treatments for aggressive microcarcinoma is selected based in part of a determination that there is one or more of: (i) an increase in a level of one or more of miR-3065-5p, miR-15b-5p, miR-1271-5p, and miR-199b-3p in a sample obtained from a subject compared to a normal or control level and (ii) a decrease in one or more of: miR-4484, miR-6780b-5p, miR-1185-1-3p, miR-3175, miR-4721, and miR-3165-5p in the sample from the subject compared to a normal or control level. As used herein, the term "normal" used in reference to tissue is used interchangeably with the term "uninvolved," and means tissue that is outside of a primary tumor. Thus, as used herein "normal tissue" means tissue that is outside and/or is obtained from outside a primary tumor area.

Assays and Assessment

Methods of the invention, in some aspects, permit assessment of characteristics of predetermined miRNAs in a sample from a cell and/or subject. Certain aspects of the invention include methods of assessing samples for predetermined miRNAS and in some aspects additional miRNAs other than the 1, 2, 3, 4, 5, 6, 7, 8, 9, 10, 11, 12, 13, 14, and 15 listed above herein. Additional miRNAs may be included as positive or negative controls or for other reasons, a practice routine in the assay arts. Methods of the invention may include contacting a sample with an agent that specifically binds to a predetermined miRNA wherein the contacting occurs under conditions suitable for the agent to bind to the miRNA in the sample. Under such conditions the agent and the miRNA may form what is referred to herein as a "bound complex", which can be detected, permitting assessment of one or more characteristics of the miRNAs in the sample. It will be understood that characteristics of an miRNA in a sample will correspond to and can be extrapolated to identify characteristics of the miRNA in the source from which the sample was obtained. In some embodiments of the invention, non-limiting examples of agents comprise: a microarray probe, a probe, a primer, a polynucleotide molecule, a detectable label, an enzyme, a buffer, a radioisotope, a dye, and an oligonucleotide. As will be understood, an agent may comprise more than one element, for example, though not intended to be limiting, an agent may include a probe and a detectable label.

With respect to characteristics of an miRNA in a sample, an assessment method of the invention that results in no detection (for example a zero amount or level) of a bound complex that normally would be formed by contacting the miRNA with the binding agent that specifically binds that miRNA under suitable conditions indicates the absence of the miRNA in the sample. Any detected bound complex that would be formed by contacting the miRNA with the binding agent that specifically binds that miRNA under suitable conditions indicates the presence of the miRNA in the sample. Additional methods of the invention may be used to determine the amount or level of an miRNA in a sample, for example, though not intended to be limiting, detecting a level of a bound complex formed following contact of the sample with an agent known to bind a miRNA, detecting a level of a predetermined miRNA, etc.

Methods and compounds of the invention that can be used to determine (also referred to herein as "to identify") a characteristic a predetermined miRNA in a sample, cell, tissue, and/or subject, may be used to identify the presence/absence or status of PMC of the thyroid in the cell, tissue, or subject. Such methods of the invention may be used in identifying PMC and the status of the PMC as indolent or aggressive PMC of the thyroid. With respect to an miRNA level in a sample, as used herein a "normal" level may be no detected miRNA as determined using a method of the invention. An "abnormal" level is defined as a level of detected miRNA that is higher than a normal level of the miRNA as determined using a method of the invention. As used herein, with respect to a level of an miRNA or agent/miRNA bound complex or other molecule described herein, the terms: "increased", "elevated", and "higher" are used interchangeably, and the terms "decrease", "reduced", and "lower" are used interchangeably.

Methods and assays set forth in certain embodiments of the invention can be used to identify the status of a PMC of the thyroid, and to evaluate and compare one or more characteristics of predetermined miRNAs in a sample, or in some embodiments of the invention, in a cell and/or subject. Methods in some aspects of the invention may include detecting in a sample one or more characteristics of a predetermined miRNA. Information obtained using methods of the invention can be used to identify the status of PMC of the thyroid in a sample, cell, and/or subject and may be used to aid in selecting a treatment for a subject found to have or to be at risk of having indolent or aggressive PMC of the thyroid.

Methods of the invention, in some embodiments, may include detecting characteristics of a predetermined miRNA in a sample and comparing the detected level to one or more of: a level of zero, a control level, and a prior level in a sample from obtained the same source. In certain aspects of the invention, a characteristic of an miRNA in a cell, cell culture, and/or a subject can be detected using methods of the invention to measure the miRNA for example, using one or more routine methods such as, but not limited to: microarray analysis, deep sequencing, polymerase chain reaction (PCR), real time PCR, northern blotting, in situ hybridization RNA-seq, and qPCR.

Controls

In some embodiments of the invention, methods may include comparing a characteristic of an miRNA in a sample to a control value of the characteristic of the miRNA. As used herein a "control" may be a normal control or a PMC control known to have miRNA characteristics of indolent PMC or known to have miRNA characteristics of aggressive PMC. Selection and use of appropriate controls in comparative, diagnostic, treatment, and assay methods are well known in the art. In some embodiments of the invention, a normal control level is the amount or level of an miRNA in a subject and/or cell that is free of PMC, indolent PMC, and/or aggressive PMC. A control level of an miRNA can readily be determined by measuring an amount or level of the miRNA using a method of the invention, as described herein or other art-known means. In some embodiments of the invention, an autoimmune disease control level may be obtained from a sample from a subject or cell known have indolent PMC or known to have aggressive PMC. In some embodiments, a control level of an miRNA may be based on levels obtained from one or more subjects and/or cells known to have indolent PMC or known to have aggressive PMC.

In some embodiments of the invention, a control characteristic of an miRNA is the characteristic of the miRNA determined from samples, cells, and/or subjects that do not have PMC, indolent PMC, and/or aggressive PMC.

Subject, Diseases, Cells, and Samples

As used herein, a subject shall mean a vertebrate animal including but not limited to a human, mouse, rat, guinea pig, rabbit, cow, dog, cat, horse, goat, and primate, e.g., monkey. In certain aspects of the invention, a subject may be a domesticated animal, a wild animal, or an agricultural animal. Thus, the invention can be used to test for and treat diseases or conditions in human and non-human subjects. For instance, methods and compositions of the invention can be used in veterinary applications as well as in human prevention and treatment regimens. In some embodiments of the invention, the subject is a human. In some embodiments of the invention, a subject has a PMC of the thyroid.

A subject at risk of having or suspected of having PMC is a subject who has been diagnosed with PMC or believed likely to have PMC based on factors such as clinical examination, symptoms, and other art-known methods to assess thyroid disease, such as PMC. For example, though not intended to be limiting, visual and/or physical examination of the neck of a subject may suggest the subject as likely to have a thyroid condition, and that condition may be PMC. Are-known diagnostics and assessments can be used to determine if a subject is a risk of having, is believed to have, is likely to have, or is diagnosed as having PMC of the thyroid.

Cells that may be assayed and/or treated using methods and compounds of the invention include but are not limited to mammalian cells, human cells, vertebrate cells, non-human mammalian cells, cultured cells, thyroid tissue cells, non-thyroid tissue cells, lymph fluid cells, blood plasma, and serum.

A sample of the invention may be referred to as a biological sample. A biological sample may include biological material, non-limiting examples of which are one or more of: tissue, cells, blood, serum, saliva, CSF fluid, and lymph fluid. Routine procedures can be used to obtain samples for use in methods of the invention and to carry out pre-testing steps such as separation, purification, or other routine preparation steps. As used herein the term "sample" and "biological sample" may be used interchangeably. In some embodiments of the invention may comprise one or more of cells and tissues obtained from a subject. One or more samples may be obtained from a subject using art-known methods, non-limiting examples of which are: resection, biopsy, blood draw, fluid draw, scraping, punch biopsy, needle biopsy, fluid collection, and surgical removal.

Information on samples, treatments, miRNA measurement, miRNA characteristic determination is available in the art and can be used in conjunction with the information provided herein, see for example: Taguchi Y-h, Murakami Y (2013) PLoS ONE 8(6): e66714. doi:10.1371/journal.pone.0066714 and van Rooij, E. (2011) Circulation Research vol 108; 219-234; the content of each of which is incorporated herein by reference in its entirety.

Treatment Methods and Compounds

Certain aspects of the invention include selecting methods and compounds to treat PMC in a subject. Examples of treatments for PMC though not intended to be limiting include one or more of: surgery, radiation, chemotherapy, administration of a pharmaceutical agent, and removal of all or a portion of the thyroid. Treatments for indolent PMC that may be selected based at least in part on results obtained using methods of the invention, include, but are not limited to one or more of: abstention from surgery, abstention from radiation, abstention from chemotherapy, and abstention from administration of a pharmaceutical agent. The prior generally practiced treatment for PMC of the thyroid included surgery and tissue removal. In contrast, methods of the invention can be used to provide an alternate treatment strategy to a subject, whereby the strategy is based at least in part, on whether the PMC is determined to be indolent or aggressive.

Embodiments of methods of the invention permit novel treatment strategies to be selected and used for subjects identified as having PMC. For example, though not intended to be limiting, for a subject with an indolent PMC, determined at least in part using a methods of the invention, selection of a treatment may include selecting to abstain from surgery, to abstain from radiation, to abstain from chemotherapy, and/or to abstain from administration of another pharmaceutical agent to treat the PMC. In another example, though not intended to be limiting, for a subject with an aggressive PMC, determined at least in part using a methods of the invention, selection of a treatment may include administering to the subject one or more of: surgical treatment, radiation treatment, chemotherapy, and another pharmaceutical agent to treat the PMC.

In some embodiments of the invention, a result of determining one or more characteristics of miRNAs in a sample using a method of the invention may confirm the presence of an indolent PMC. If the sample was obtained from a subject, the results confirming the presence of an indolent PMC can assist in identifying the subject as having an indolent PMC. It will be understood that in certain embodiments of the invention, a result of determining one or more characteristics of miRNAs in a sample using a method of the invention can indicate that a signature for an aggressive PMC is not present in the sample and thus the result may exclude an aggressive PMC. If the sample was obtained from a subject, the results excluding the presence of an aggressive PMC can assist in identifying the subject as not having an aggressive PMC, which can aid in selecting a treatment for an indolent PMC in the subject. Non-limiting examples of treatments for indolent PMC are provided elsewhere herein. Thus, a treatment for a subject may be selected at least in part based on use of methods of the invention that confirm an "indolent" signature and/or that exclude an aggressive PMC signature based on the sample results.

Kits

The invention also encompasses kits for detecting characteristics and properties of miRNAs and/or bound complexes of miRNAs and agents that specifically bind the miRNAs. For example, a kit can comprise a labeled or labelable agent capable of aiding in detecting and assessing an miRNA in a sample and a means for determining a status (e.g., at least one of the presence/absence, and level) of the miRNA in the sample. The agent can be packaged in a suitable container. The kit can further comprise a means for comparing the presence/absence and/or level of one or more miRNAs in the sample with a standard or control and/or can further comprise instructions for using the kit to detect the presence/absence and level of the one or more miRNAs. A kit may also include a detectable agent that specifically binds a predetermined miRNA. Thus, some embodiments of the invention provide kits that can be used to detect and assess the presence/absence and/or level of an miRNA, including, but not limited to one or more of: miR-146b, miR-138-1-3p, miR-3065-5p, miR-15b-5p, miR-1271-5p, miR-199b-3p, miR-4484, miR-6780b-5p, miR-1185-1-3p, miR-3175, miR-4721, miR-3165-5p, miR-16-5p, miR-1991-3p, and miR-96-5p and may be used to determine a status of PMC in a subject as indolent or aggressive. Kits of the invention may also include detectable labels, enzymes, buffers, containers, and other items for use in carrying out methods of the invention.

A kit of the invention may also include instructions. Instructions typically will be in written form and will provide guidance for carrying out the preparation and procedure for one or more methods of the invention.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Examples 1-4

Introduction

Two unique cohorts of papillary microcarcinoma of the thyroid gland; one indolent and one aggressive with massive metastases at the time of diagnosis are currently available for studies described in Examples 1-4. The significance of these studies is that in refining the understanding of the pathogenesis of PMC, novel diagnostic and therapeutic approaches can be utilized that reduce unnecessary surgeries and ultimately improve therapeutic outcomes for patients diagnosed with papillary microcarcinomas. Methods described under this Example also apply to remaining examples. Sequences of miRNAs assessed in the Examples are available at miRBASE, http://mirbase.org/.

Example 1

To assess distinct molecular mechanisms underlying indolent and aggressive papillary microcarcinoma (PMC) of the thyroid, analysis of short noncoding (ncRNA) profiles was performed.

Materials/Methods

Comparative ncRNA analysis was performed using Affymetrix GeneChip® miRNA 4.0 Array, (Affymetrix, Santa Clara, CA) according to manufacturer's protocols, on RNA extracted from 17 cases of PMC (<45 y/o cohort: 7 cases—3 indolent PMC, 4 aggressive PMC) (>45 y/o cohort: 10 cases—5 indolent, 5 aggressive). Bioinformatics analyses included multivariate Principal Component Analysis to identify sample-based differential expression and univariate linear modeling of sample groups to detect gene-based differential expression.

Results

In indolent primary tumors (T), 18 ncRNAs were found to be significantly altered compared with matched normal tissue (N); 34 ncRNAs were altered in aggressive primary tumors (AT) compared with normal (AN). Of those 52 ncRNAs, 9 are unique to T and 25 unique to AT (FIG. 1, Panel A). Direct comparison of miR profiles in AT versus T revealed 12 miRs significantly altered which target 622 mRNAs associated with tumorigenesis. These include miR-16-5p, miR-1991-3p, miR-96-5p whose targets include MAPK, RAS, PI3K, WNT and pluripotency transcription factors including NANOG. Analysis of aggressive tumors revealed distinct profiles of AN vs AT vs AM. Of note, in AM (FIG. 1, Panel B), 410 ncRNAs were found to be significantly altered compared with the AT primary site indicating a distinct molecular profile in the metastatic site.

These results indicated distinct molecular profiles characterizing indolent and aggressive PMCs which can be used to aid in diagnosis and therapeutic interventions in PMC of the thyroid.

Example 2

Comparative ncRNA analyses were performed using Affymetrix GeneChip® miRNA 4.0 Array, (Affymetrix, Santa Clara, CA) according to manufacturer's protocols, on RNA extracted from 17 cases of PMC (<45 y/o cohort: 7 cases—3 indolent PMC, 4 aggressive PMC) (>45 y/o cohort: 10 cases—5 indolent, 5 aggressive). Bioinformatics analyses included multivariate Principal Component Analysis to identify sample-based differential expression and univariate linear modeling of sample groups to detect gene-based differential expression.

Results showed altered levels of two miRNAs, miR-146b and miR-138-1-3p. It was determined that an increase in the level of miR-146b compared to a normal or control level and a decrease in level of miR-138-1-3p compared to a normal or control level identified indolent tumor. In addition, results showed altered levels of 7 additional miRNAs, miR-3065-5p, miR-4484, miR-6780b-5p, miR-1185-1-3p, miR-3175, miR-4721, and miR-3165-5p. It was determined that an increase in the level of miR-3065-5p compared to a normal or control level and a decrease in level of miR-4484, miR-6780b-5p, miR-1185-1-3p, miR-3175, miR-4721, or miR-3165-5p compared to normal or control level identified aggressive tumor (FIG. 2).

Figure 2:
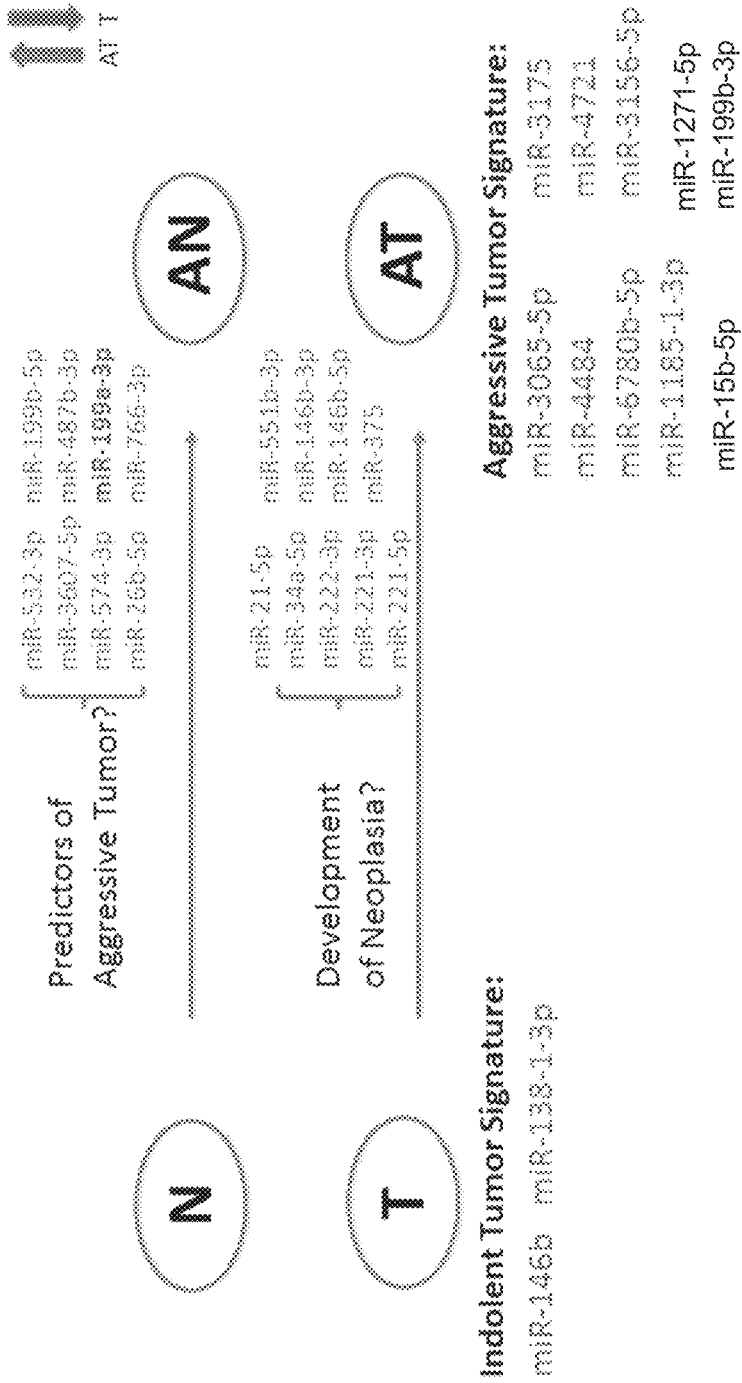

The results supported use of identifying the presence or absence and/or a level of one or more of the miRNAs: miR-146b, miR-138-1-3p, miR-3065-5p, miR-4484, miR-6780b-5p, miR-1185-1-3p, miR-3175, miR-4721, miR-3165-5p as "signatures" for different types of PMC of the thyroid and for use to aid in selecting an appropriate treatment for a PMC (see FIG. 2).

Results also indicated that miR-146B-5P and miR-221/222 were increased (upregulated) in indolent and aggressive; and miR-16 and miR-613 levels were not altered in either indolent or aggressive, compared to normal control levels.

Example 3

A sample is obtained from a subject and characteristics of miRNAs in the sample are determined and compared to control characteristics of the miRNAs. One or more of the following are determined: an increase in the level of miR-146b in the sample and a decrease in level of miR-138-1-3p in the sample. Based in at least in part on these results a treatment is selected for the subject. The treatment includes abstaining from thyroid removal or thyroid lobe removal surgery.

Example 4

A sample is obtained from a subject and characteristics of miRNAs in the sample are determined and compared to control characteristics of the miRNAs. One or more of the following are determined: an increase in the level of miR-3065-5p in the sample and a decrease in level of one or more of: miR-4484, miR-6780b-5p, miR-1185-1-3p, miR-3175, miR-4721, and miR-3165-5p. Based in at least in part on these results a treatment is selected for the subject. The treatment comprises thyroid removal or thyroid lobe removal surgery.

Example 5

Additional resection samples were obtained and characteristics of miRNAs in the samples were determined and compared to control characteristics of the miRNAs. The additional resection samples were processed using RNA-seq methods and the resulting data assessed as described in Examples 1-4. The RNAseq results were used to confirm the targets of changed miRNAs, and not the miRNAs themselves. An orthogonal technique, qPCR, was used to confirm certain of the microarray results (see Examples 1-4 for microarray studies). Results of certain of the qPCR experiments are shown in FIG. 3A-B and FIG. 4A-F.

For the RNA-seq methods, RNAseq libraries were built using an RNAseq kit: KAPA Stranded RNA-Seq Kit with RiboErase (HMR) (Catalog #KK8483 from Kapa Biosystems; Wilmington, MA) according to the manufacturer's instructions. Sequencing was performed using Illumina NextGen Sequencing according to the manufacturer's instructions (Illumina, San Diego, CA). An Illumina HiSeq 1500 sequencer was used for RNAseq procedures (Illumina, San Diego, CA).

The qPCR procedures were performed using TaqMan Fast Advanced Master Mix according to the manufacturer's instructions and samples were assayed using Applied Biosystems QuantStudio3 according to the manufacturer's instructions. (Applied Biosystems, Foster City, CA)

The results obtained from these resection samples confirmed the PMC signatures obtained in microarray experiments outlined in Examples 1~4 and also demonstrated three additional microRNAs as indicative of an aggressive signature. Overall results are set forth in Table 1, which shows results of data analysis from assessment of miRNAs in resection samples and includes results obtained using microarray procedures and analysis (see Examples 1-4) and the RNA-seq and qPCR procedures and analysis. The first column shows increased miRNAs in biopsies from indolent PMC tissues and the second column shows decreased miRNAs in biopsies from indolent PMC tissues. The third column shows increased miRNAs determined in biopsies from Aggressive PMC tissues and the fourth column shows decreased miRNAs determined in biopsies from Aggressive PMC tissues.

TABLE 1

Identification of PMC signatures.

| INDOLENT TISSUES | | AGGRESSIVE TISSUES | |
|---|---|---|---|
| Increased in Tumor | Decreased in Tumor | Increased in Tumor | Decreased in Tumor |
| miR-146b | miR-138-1-3p * | miR-3065-5p | miR-4484 |
| | | | miR-6780b-5p |
| | | | miR-1185-1-3p |
| | | | miR-3175 *** |
| | | | miR-4721 |
| | | | miR-3156-5p |
| | | miR-15b-5p ** | |
| | | miR-1271-5p ** | |
| | | miR-199b-3p ** | |

* using microarray miR-138-1-3p microRNA was identified as a component of the indolent signature and the decreased level was not detected in the qPCR protocols used in the later experiments.
** three additional microRNAs determined to be increased in aggressive PMC tissues;
*** miR-3175 microarray results were not evaluated using RNA-seq methods.

Figure 3A:
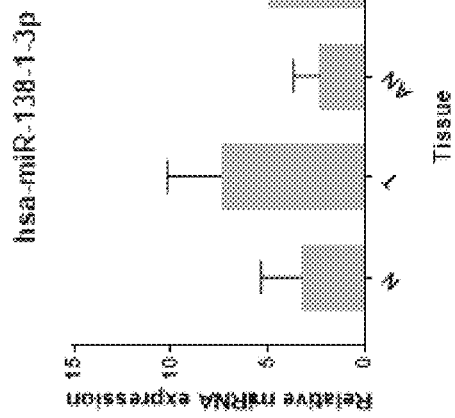
FIG. 3A-B provides graphs of results of studies to determine expression of miRNAs: hsa-miR-146-5p FIG. 3A) and hsa-miR-138-1-3 (FIG. 3B).
Figure 3B:
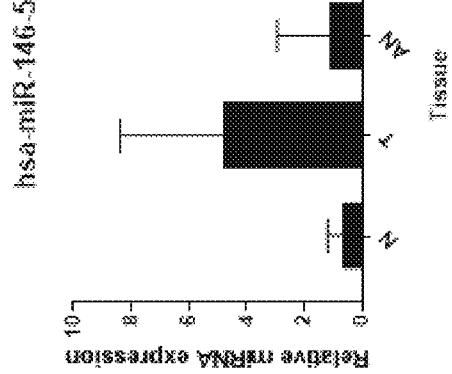
Figure 4A:
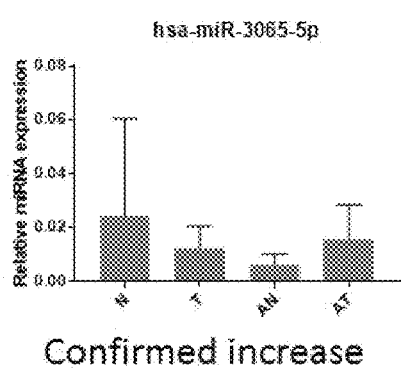
FIG. 4A-F provides graphs of results of studies to determine expression of miRNAs: hsa-miR-3065-5p, (FIG. 4A); hsa-miR-4484 (FIG. 4B); hsa-miR-6780-5p (FIG. 4C); and hsa-miR-1185 (FIG. 4D); hsa-miR-3156-5p (FIG. 4E); and hsa-miR-4721 (FIG. 4F). "T" is indolent primary tumor tissue and "N" is the matched normal tissue. "AT" is aggressive primary tumor tissue and "AN" is the matched normal tissue.
Figure 4B:
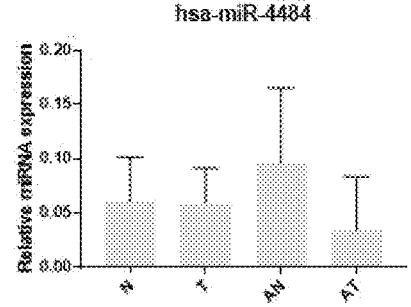
Figure 4C:
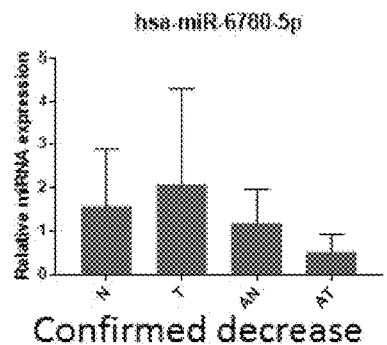
Figure 4D:
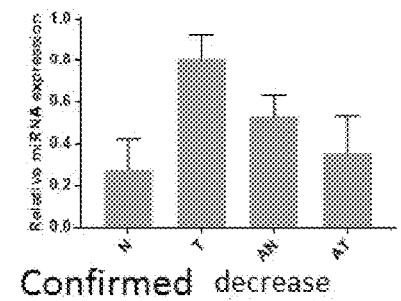
Figure 4E:
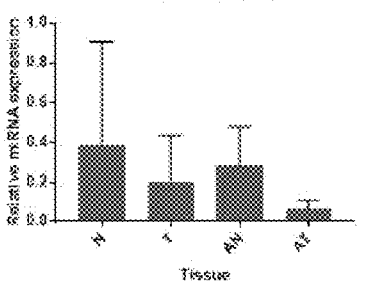
Figure 4F:
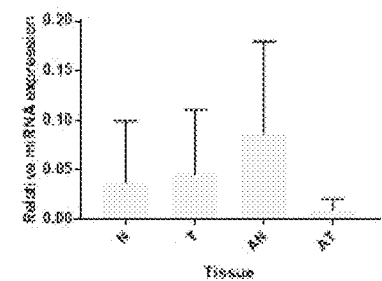

The study included biopsies from indolent PMC tumors with matched uninvolved tissues and biopsies from aggressive PMC tumors with matched uninvolved tissues. The samples were analyzed by RNA-seq methods (see for example, Wang, J. et al., Nature Reviews Genetics vol. 10, 57-63, 2009) and changes in target RNA expression and associated cell pathways were identified. The differential RNA expression was mapped to the altered microRNAs from the signatures. Graphs provided in FIG. 3A-B show indolent signature and graphs provided in FIG. 4A-F show aggressive signature. The experimental results from Examples 1-5 confirmed the signature identification.

The undertaken analysis identified regulatory microRNAs in the signatures. Some technical validation of the microarray analyses, which generated the original signatures (see Examples 1-4 above herein), was limited by the availability of remaining tissue/RNA sample, and the variability level reflected the small sample size and the limited RNA. Nevertheless, the results from the RNA-seq and qPCR experiments confirmed the direction of change identified in the prior experiments, (see Examples 1-4 herein) and results identifying the PMC signatures are summarized in Table 1.

Example 6

A sample is obtained from a subject and using methods described in Examples 1-5 and elsewhere herein, an indolent PMC signature is determined in the sample and the subject is identified as having an indolent PMC. A treatment for the subject is selected at least in part based on confirmation of the "indolent" determination and/or on the exclusion of an aggressive PMC signature based on the sample results. The selected treatment includes one or more of: abstention from surgery, abstention from radiation therapy, abstention from chemotherapy, and abstention from administration of another pharmaceutical agent to treat the PMC. The subject is treated with the selected therapy.

Example 7

A sample is obtained from a subject and using methods described in Examples 1-5 and elsewhere herein, an aggressive PMC signature is determined in the sample and the subject is identified as having an aggressive PMC. A treatment for the subject is selected at least in part based on the "aggressive" determination and the selected treatment includes one or more of surgical therapy, radiation therapy, chemotherapy, and administration of a pharmaceutical agent to treat the PMC. The subject is treated with the selected therapy.

Equivalents

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

What is claimed is:

1. A method of selecting a treatment for a subject, comprising:
    (a) obtaining a biological sample from a subject believed at risk for an aggressive signature papillary microcarcinoma of the thyroid;
    (b) contacting the biological sample with one or more agents that bind to one or more of microRNAs (miRs): miR-3065-5p, miR-15b-5p, miR-1271-5p, miR-199a-3p, miR-199b-5p, miR-4484, miR-6780b-5p, miR-3175, miR-3156-5p, miR-1185-1-3p, miR-1356-5p, and miR-4721;
    (c) determining presence of binding of the one or more agents with the one or more miRs and determining a level of the one or more miRs determined as present in the sample;
    (d) comparing the determined level of the miRs with a control level of the miRs that does not indicate an aggressive papillary microcarcinoma signature, wherein
    (i) a determined level of one or more of miR-4484, miR-6780b-5p, miR-3175, miR-3156-5p, miR-1185-1-3p, miR-1356-5p, and miR-4721 that is lower than the control level of the miR-4484, miR-6780b-5p, miR-3175, miR-3156-5p, miR-1185-1-3p, miR-1356-5p, and miR-4721, respectively, identifies an aggressive signature papillary microcarcinoma of the thyroid in the subject, and
    (ii) a determined level of miR-3065-5p, miR-15b-5p, miR-1271-5p, miR-199a-3p, miR-199b-5p, that is higher than the control level of the miR-3065-5p, miR-15b-5p, miR-1271-5p, miR-199a-3p, and miR-199b-5p, respectively, identifies an aggressive signature of the microcarcinoma of the thyroid;
    (e) selecting a treatment for the subject based at least in part on the identified aggressive signature papillary microcarcinoma of the thyroid in the subject; wherein the selected treatment comprises one or more of: thyroid removal surgery, thyroid lobe removal surgery, and administration of one or more of: radiation, chemotherapy, and a pharmaceutical agent that treats a papillary microcarcinoma of the thyroid; and
    (f) administering the selected treatment to the subject.

2. The method of claim 1, wherein a level of binding of one or more of miR-3065-5p, miR-15b-5p, miR-1271-5p, miR-199a-3p, miR-199b-5p, miR-4484, miR-6780b-5p, miR-3175, miR-3156-5p, miR-1185-1-3p, miR1356-5p, and miR-4721 greater than zero determines the presence of the one or more miRs, respectively, and a level of binding of one or more of miR-3065-5p, miR-15b-5p, miR-1271-5p, miR-199a-3p, miR-199b-5p, miR-4484, miR-6780b-5p, miR-3175, miR-3156-5p, miR-1185-1-3p, miR1356-5p, and miR-4721 equal to zero determines that the miRNA, respectively, is not present in the biological sample.

3. The method of claim 1, wherein the subject is a mammal.

4. The method claim 1, further comprising determining in the biological sample one or more of (i) presence or absence and (ii) a level of an miRNA that is not one of miR-3065-5p, miR-15b-5p, miR-1271-5p, miR-199a-3p, miR-199b-5p, miR-4484, miR-6780b-5p, miR-3175, miR-3156-5p, miR-1185-1-3p, miR-1356-5p, and miR-4721 and optionally using the determination to aid in the treatment selection.

5. The method of claim 4, further comprising treating the subject with the selected treatment.

6. The method claim 4, wherein the determining comprises determining in the biological sample one or more of (i) presence or absence and (ii) a level of one or more of -146b-3p, miR-146b-5p, miR-138-1-3p, miR-3156-5p, miR-16-5p, miR-199a-3p, miR-96-5p, miR-15b-5p, miR-1271-5p, miR-199b-5p, miR-532-3p, miR-3607-5p, miR-574-3p, miR-26b-5p, miR-487b-3p, miR-766-3p, miR-21-5p, miR-34a-5p, miR-222-3p, miR-221-3p, miR-221-5p, miR-551b-3p, and miR-375 and optionally using the determination to aid in the treatment selection.

7. The method of claim 1, wherein the subject is a human.

* * * * *

UNITED STATES PATENT AND TRADEMARK OFFICE
CERTIFICATE OF CORRECTION

| | | |
|---|---|---|
| PATENT NO. | : 12,371,749 B2 | Page 1 of 1 |
| APPLICATION NO. | : 17/515938 | |
| DATED | : July 29, 2025 | |
| INVENTOR(S) | : Frances Carr and Nikoletta Sidiropoulos | |

It is certified that error appears in the above-identified patent and that said Letters Patent is hereby corrected as shown below:

In the Claims

Column 18, In Claim 6, Line 31, please replace "-146b-3p," with --miR-146b-3p,--.

Signed and Sealed this
Thirtieth Day of September, 2025

John A. Squires
*Director of the United States Patent and Trademark Office*